(12) United States Patent
Oda (10) Patent No.: US 8,998,607 B2
(45) Date of Patent: Apr. 7, 2015

(54) SELF-LIGATING ORTHODONTIC BRACKET HAVING UNDERCUTS AND RELATED METHODS

(75) Inventor: Todd I. Oda, Torrance, CA (US)

(73) Assignee: Ormco Corporation, Orange, CA (US)

(*) Notice: Subject to any disclaimer, the term of this patent is extended or adjusted under 35 U.S.C. 154(b) by 0 days.

(21) Appl. No.: 13/303,600

(22) Filed: Nov. 23, 2011

(65) Prior Publication Data

US 2012/0129119 A1   May 24, 2012

Related U.S. Application Data

(60) Provisional application No. 61/416,922, filed on Nov. 24, 2010.

(51) Int. Cl.
*A61C 3/00* (2006.01)
*A61C 7/28* (2006.01)

(52) U.S. Cl.
CPC ...................................... *A61C 7/287* (2013.01)

(58) Field of Classification Search
USPC ...................... 433/10–14, 16, 18, 8, 9, 15, 17
See application file for complete search history.

(56) References Cited

U.S. PATENT DOCUMENTS

| | | | | |
|---|---|---|---|---|
| 4,941,825 A * | 7/1990 | Lerner | ............................ | 433/14 |
| 6,168,428 B1 * | 1/2001 | Voudouris | ....................... | 433/11 |
| 6,190,166 B1 * | 2/2001 | Sasakura | ......................... | 433/14 |
| 2005/0239012 A1 * | 10/2005 | Bathen et al. | .................. | 433/10 |
| 2007/0248928 A1 * | 10/2007 | Damon | ............................ | 433/10 |
| 2007/0259304 A1 * | 11/2007 | Hagelganz et al. | ............. | 433/10 |

* cited by examiner

*Primary Examiner* — Cris L Rodriguez
*Assistant Examiner* — Mirayda A Aponte
(74) *Attorney, Agent, or Firm* — Wood, Herron & Evans, LLP (57) ABSTRACT

A method of manufacturing an orthodontic appliance may include molding a plurality of green bodies in plurality of molds and coupling the green bodies so as to form an intermediate green body. The orthodontic appliance may be an orthodontic bracket body. The plurality of green bodies may be molded so as to be devoid of any undercut formations. Coupling the plurality of green bodies may form the intermediate green body to include at least one undercut formation. An orthodontic bracket may include an undercut formation not capable of being formed in a single shot molding process and not formed through post-formation processes. The undercut formation may include a guiding track and/or a retaining recess configured to receive a portion of the ligating member. The ligating member may include a flexible ligating portion that overlies the archwire slot and a relatively rigid main body portion.

20 Claims, 8 Drawing Sheets

SELF-LIGATING ORTHODONTIC BRACKET HAVING UNDERCUTS AND RELATED METHODS

CROSS REFERENCE TO RELATED CASES

This application claims priority to U.S. Provisional Patent Application Ser. No. 61/416,922 filed Nov. 24, 2010, the disclosure of which is incorporated by reference herein in its entirety.

TECHNICAL FIELD

The present invention relates generally to orthodontic brackets and, more specifically, to self-ligating orthodontic brackets having undercuts and methods for making orthodontic brackets having such undercuts.

BACKGROUND

Orthodontic brackets are a component of orthodontic systems for correcting malpositioned teeth. Orthodontic treatment using such systems generally involves the application of mechanical forces to urge malpositioned teeth into correct alignment. In conventional treatment, orthodontists or their assistants affix orthodontic brackets to a patient's teeth and engage an archwire into an archwire slot in each bracket. The archwire applies mechanical forces that coerce the teeth to move into a desired position. Traditionally, ligatures are employed to retain the archwire within each bracket's archwire slot. But ligatures may be difficult to handle and apply so as to secure the archwire to the brackets. To overcome these difficulties, self-ligating orthodontic brackets have been developed that eliminate the need for separate, individual ligatures by relying on a movable ligating member on the bracket, such as a latch or a slide, which in a closed position overlies the archwire slot thereby retaining the archwire within the bracket's archwire slot. In this regard, the bracket body may include a track or passageway configured to receive the ligating member therein and facilitate the movement of the ligating member between an opened and closed position.

Conventional manufacturing processes for orthodontic brackets include metal injection molding (MIM) and ceramic injection molding (CIM) for metal and ceramic brackets, respectively. In each of these processes, metal or ceramic particles are mixed with a binder and then injected into a mold having the shape of an orthodontic bracket. The intermediate body resulting from the molding process is typically oversized compared to the final product. The intermediate body is then sintered to remove the binder and form either a metal or ceramic orthodontic bracket. The intermediate body typically shrinks during the sintering process to arrive at the desired size of the orthodontic bracket.

The conventional molding process in the MIM or CIM process is typically a single shot process. Thus, the configuration of the various features of the orthodontic bracket may be limited by such a single shot molding process. In this regard, various features of the bracket, including, for example, the archwire slot, the passageway for the ligating member, an overshoot cavity configured to capture an end of the ligating member, or other features may not be capable of being formed from a single shot molding process. Accordingly, these features, if desired in the orthodontic bracket, are typically formed through a post-formation process. Such post-formation processes are generally time consuming and expensive.

Some molding apparatus have increased in their complexity and may include a movable slide extendable from the wall of the mold cavity and capable of moving into and out of the mold cavity so as to form various features in the molded body. Because the slide must be retractable from the mold cavity, or ultimately the molded body must be de-molded from the mold cavity, the slide has limited geometries. For example, the more distal portions of the slide (i.e., portions further from the wall of the mold cavity) must be narrower than more proximal portions of the slide (i.e., portions closer to the wall of the mold cavity).

This converging aspect in a proximal to distal direction then allows the slide to be retracted from the mold cavity, or allows the molded body to be de-molded from the mold cavity. In contrast, a diverging geometry (i.e., wider in a more distal direction) would not allow the slide to be retracted, or allow the molded body to be de-molded from the mold cavity. This limitation in the single shot molding process then limits the possible geometries of the bracket features capable of being formed by such movable slides. However, such alternative geometries of orthodontic bracket features not capable of being formed in a single shot molding process may be desirable to enhance use and functionality of the orthodontic bracket. For example, certain undercut formations, which include various voids or cavities, are not capable of being formed in a single shot molding process and thus are typically formed using post-formation processes.

There is a need, therefore, for self-ligating orthodontic brackets and associated methods for forming self-ligating orthodontic brackets that address these and other problems associated with conventional orthodontic brackets and manufacturing methods. More particularly, there is a need for an orthodontic bracket having undercuts or other features not capable of being formed in a single shot molding process and a method for making such an orthodontic bracket that avoids the high cost and increased time of making such undercuts or other features in post-formation processes.

SUMMARY OF THE INVENTION

In one embodiment, a method of manufacturing an orthodontic appliance comprises molding a plurality of bodies in a respective plurality of molds to form a plurality of green bodies. The method further includes coupling the plurality of green bodies so as to form a single intermediate green body having the shape of the orthodontic appliance and sintering the intermediate green body to form the orthodontic appliance. In one embodiment, the orthodontic appliance is an orthodontic bracket body. In one embodiment, the method further comprises molding the plurality of green bodies so as to be devoid of any undercut formations. In one embodiment, the method further comprises coupling the plurality of green bodies such that the intermediate green body includes at least one undercut formation.

In one embodiment of the invention, an orthodontic bracket comprises a bracket body configured to be mounted onto a tooth. The bracket body includes an archwire slot adapted to receive an archwire therein and a ligating member coupled to the bracket body and movable relative thereto between an opened position in which the archwire may be received into the archwire slot, and a closed position in which the ligating member overlies the archwire slot and retains the archwire in the archwire slot. The bracket body includes at least one undercut formation therein not capable of being formed in a single shot molding process and not formed through post-formation processes.

In one embodiment, the undercut formation includes a guiding track configured to receive the ligating member therein during movement between the opened position and the closed position and including a first portion having a first width and a second portion have a second width greater than the first width.

In one embodiment, the undercut formation includes a retaining recess configured to receive a portion of the ligating member when the ligating member is in the closed position.

In one embodiment, the ligating member includes a flexible ligating portion that overlies the archwire slot in the closed position and a relatively rigid main body portion coupled to the flexible ligating portion.

In one embodiment, the ligating member includes a resilient ligating portion capable of flexing between an expanded position and a contracted position, and the bracket body includes a guiding track having a first portion defined by a first pair of walls and a second portion defined by a second pair of walls, the first portion having a first width less than a second width of the second portion. In one embodiment, movement of the ligating member from the closed position to the opened position causes the ligating portion to flex from the expanded position to the contracted position.

In one embodiment, an orthodontic bracket comprises a bracket body configured to be mounted onto a tooth. The bracket body includes an archwire slot adapted to receive an archwire therein. The bracket body further includes a guiding track having a first portion and a second portion having a width greater than a width of the first portion, and a ligating member coupled to the bracket body and movable relative thereto between an opened position in which the archwire may be received into the archwire slot, and a closed position in which the ligating member overlies the archwire slot and retains the archwire in the archwire slot, the ligating member having a relatively rigid main body portion and a resilient ligating portion, the resilient ligating portion overlying the archwire slot when in the closed position. The ligating portion is capable of flexing between an expanded position and a contracted position. The ligating portion being in the expanded position when in the second portion of the guiding track and being in the contracted position when in the first portion of the guiding track.

BRIEF DESCRIPTION OF THE DRAWINGS

The accompanying drawings, which are incorporated in and constitute a part of this specification, illustrate embodiments of the invention and, with the general description given above, together with the detailed description given below, serve to explain various aspects of the invention.

DETAILED DESCRIPTION

Referring now to the drawings and specifically to FIGS. 1-5, an exemplary orthodontic bracket 10 includes a bracket body 12 and a ligating member 14 that engages with the bracket body 12. In this embodiment, the ligating member 14 is slidable relative to the bracket body 12. The bracket body 12 includes an archwire slot 16 formed therein which is adapted to receive an archwire 18 (shown in phantom) for applying corrective forces to the teeth. The ligating member 14 slides relative to the bracket body 12 between an opened position (FIG. 3) in which the archwire 18 is insertable into the archwire slot 16, and a closed position (FIG. 2) in which the ligating member 14 overlies the archwire slot 16 and retains the archwire 18 therein. As will be described in more detail below, the orthodontic bracket 10, and more particularly the bracket body 12 thereof, is formed through a molding process and includes a number of features which otherwise cannot be formed through the single shot molding process used in conventional processes. Additionally, these features in orthodontic bracket 10 are formed during the formation process and therefore avoid the drawbacks of post-formation processes.

The orthodontic bracket 10, unless otherwise indicated, is described herein using a reference frame attached to a labial surface of a tooth on the lower jaw. Consequently, as used herein, terms such as labial, lingual, mesial, distal, occlusal, and gingival used to describe the orthodontic bracket 10 are relative to that chosen reference frame. The embodiments, however, are not limited to the chosen reference frame and descriptive terms, as those of ordinary skill in the art will readily appreciate that the orthodontic bracket 10 may be used on other teeth and in other orientations within the oral cavity. For example, the bracket 10 may alternatively be coupled to the lingual surface of the tooth and be within the scope of the invention. Those of ordinary skill in the art will recognize that the descriptive terms used herein may not directly apply when there is a change in reference frame. Nevertheless, embodiments of the invention are intended to be independent of location and orientation within the oral cavity and the relative terms used to describe embodiments of the orthodontic bracket 10 are used to merely provide a clear description of the embodiments in the drawings. As such, the relative terms labial, lingual, mesial, distal, occlusal, and gingival are in no way intended to limit the invention to a particular location or orientation.

When mounted to the labial surface of a tooth on the patient's lower jaw, the bracket body 12 generally includes a lingual side 20, an occlusal side 22, a gingival side 24, a mesial side 26, a distal side 28 and a labial side 30. The lingual side 20 of the bracket body 12 is configured to be secured to the tooth in any conventional manner, such as by suitably chosen orthodontic cement or adhesive, by a band around an adjacent tooth, or other suitable methods of securement. The bracket body 12 includes a base surface 32 and a pair of opposed slot surfaces 34, 36 projecting labially from the base surface 32 that collectively define the archwire slot 16 extending in a mesial-distal direction from mesial side 26 to distal side 28. The slot surfaces 34, 36 and base surface 32 are substantially encapsulated or embedded within the material of the bracket body 12. The archwire slot 16 of the bracket body 12 may be designed to receive the orthodontic archwire 18 in any suitable manner. Although not shown, in some embodiments, the lingual side 20 of the bracket body 12 may include a pad to be used as a bonding base to facilitate coupling of the orthodontic bracket 10 to the tooth. The pad may be coupled to the bracket body 12 as a separate piece or element, or alternatively, the pad may be integrally formed with the bracket body 12.

With continued reference to FIGS. 1-5, the bracket body 12 also includes a generally planar support surface 38 adjacent and gingival of slot surface 36, and a pair of walls or projections 40, 42 that are coupled to the support surface 38 adjacent mesial and distal sides 26, 28, respectively. The support surface 38 and the projections 40, 42 jointly define a guiding track 44 of the bracket body 12. Each of the projections 40, 42 has a generally L-shaped cross section and includes a first leg projecting labially from the support surface 38, and a second leg projecting respectively in the distal and mesial directions. The projections 40, 42 partially overlie the support surface 38 in a spaced relation. The projections 40, 42 define lingual surfaces 40a, 42a and, along with support surface 38, restrict labial-lingual movement of the ligating member 14 during sliding movement thereof, relative to the bracket body 12, between the opened and closed positions.

Figure 4:
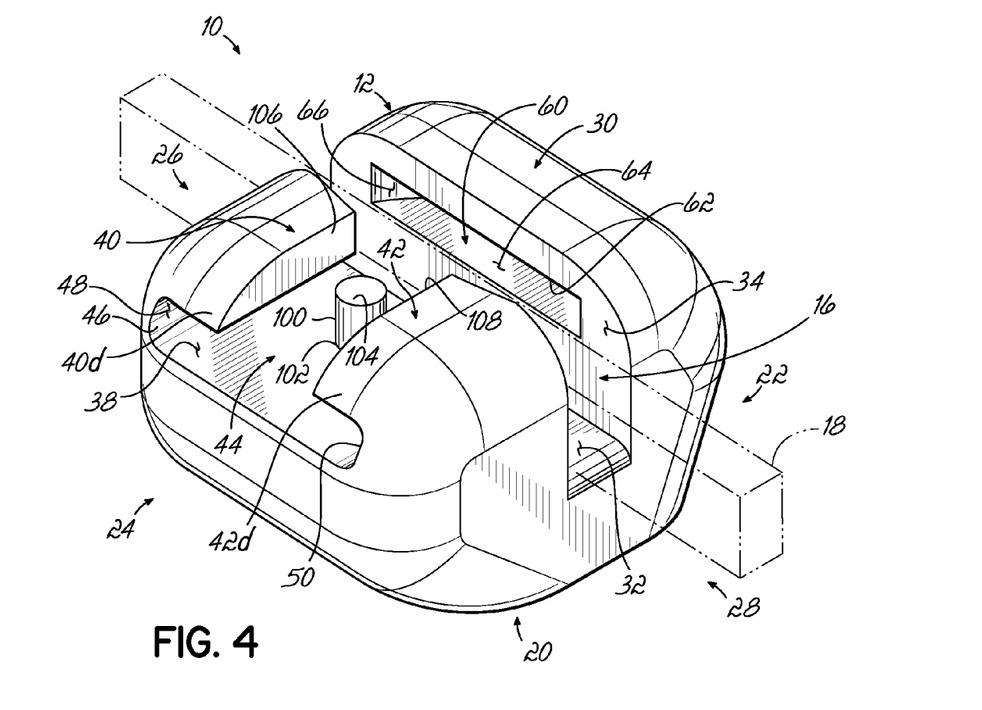
FIG. 4 is another perspective view of the bracket body of the self-ligating orthodontic bracket of FIGS. 1-3, but with the ligating member omitted.
Figure 5:
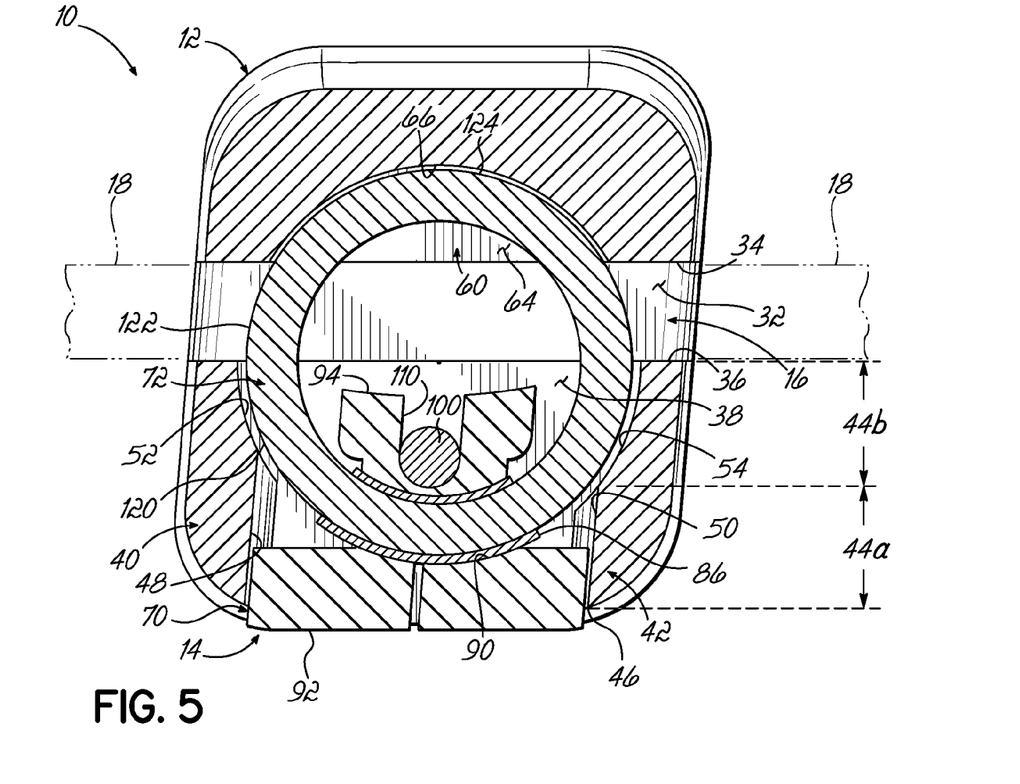
FIG. 5 is a cross-sectional view of the self-ligating orthodontic bracket of FIG. 2 taken generally along line 5-5.

In one aspect in accordance with embodiments of the invention, the guiding track 44 has a variable mesial-distal width in a direction from an opening 46 (FIG. 4) in gingival side 24 toward the archwire slot 16 (i.e., in a gingival-occlusal direction). More particularly, the guiding track 44 has a Y-shaped configuration including a generally constant width portion 44a defined by projection mesial and distal side walls 48, 50 (FIG. 5), which may be generally parallel to one another, and a wider arcuate portion 44b defined by projection mesial and distal side walls 52, 54 (FIG. 5). The constant width portion 44a is adjacent the gingival side 24 and the wider arcuate portion 44b is positioned more internal to the bracket body 12 and adjacent archwire slot 16. The arcuate portion 44b results from forming "undercuts" in the projecting mesial and distal side walls 52, 54 thereby making the guiding track 44 wider in the region of the undercuts. By this configuration, the side wall 52, 54 may correspond in shape to a portion of the ligating member 14.

It should be recognized that the formation of the undercuts in the guiding track 44 results in a configuration that diverges in a direction away from a surface of the bracket body 12 (i.e., diverges in a direction away from gingival side 24). As was discussed above, it is just such a configuration that cannot be formed in a single shot molding process typically used in conventional orthodontic bracket manufacturing. Thus, if such a Y-shaped guiding track 44 were desired in an orthodontic bracket, various post-formation processes would have to be used. As will be discussed in more detail below, in accordance with an aspect of the invention, the Y-shaped guiding track 44 may be formed in orthodontic bracket 10 during the formation process. The purpose of the Y-shaped guiding track 44 will become clearer with a more detailed discussion of the particular ligating member 14 used in conjunction with bracket body 12.

Before turning to the details of the ligating member 14, however, additional features in bracket body 12 will be described. In this regard, the occlusal archwire slot surface 34 may include a retaining recess 60 (FIGS. 4 and 5) that operates as a ligating member overshoot cavity as well as a stop mechanism that restricts movement of the ligating member 14 in a labial and gingival direction. In other words, retaining recess 60 allows the occlusal end of the ligating member 14 to extend beyond the archwire slot surface 34 and be retained therein. Thus, for example, the retaining recess 60 and the guiding track 44 may generally lie along a common plane, although not being so limited. In an exemplary embodiment, the retaining recess 60 may be defined by opposing recess surfaces 62, 64 extending occlusally from the slot surface 34, and an arcuately-shaped end surface 66 extending between the recess surfaces 62, 64 (FIGS. 4 and 5).

As will be discussed in more detail below, in one embodiment, the arcuate surface 66 of the retaining recess 60 may include a substantially constant radius of curvature (e.g., a portion of a circle) so as to conform with a similarly shaped occlusal end of the ligating member 14. In alternative embodiments, retaining recess 60 may include additional surfaces depending on the particular geometry of the ligating member 14, but nevertheless may correspond in shape to the occlusal end of the ligating member 14 configured to be received in recess 60. Thus, retaining recess 60 may have other shapes and should not be limited to the particular configuration shown and described herein. In any event, the retaining recess 60, and particularly the recess surfaces 62, 64, may be configured to further restrict labial-lingual movement of the ligating member 14 when in the closed position.

Although the particular design of the retaining recess 60 does not necessarily have the same technical issues as the Y-shaped guiding track 44 in terms of formation during a single shot molding process, its particular positioning in bracket body 12 makes the formation thereof in a single shot molding process difficult, if not impossible. More particularly, due to the positioning of retaining recess 60 in bracket body 12, a slide cannot be positioned within the mold apparatus so as to extend into the mold cavity and result in the formation of retaining recess 60. Thus, if such a retaining recess were desired in an orthodontic bracket, various post-formation processes would have to be used for its formation. Similar to above, and as will be discussed in more detail below, in accordance with an aspect of the invention, the retaining recess 60 may also be formed in orthodontic bracket 10 during the formation process. For purposes of the present application, the retaining recess 60 may also be viewed as an undercut formed in the bracket body 12.

Turning now to the ligating member 14, as illustrated in FIGS. 1-3 and 5, in one embodiment the ligating member 14 has a hybrid design including a relatively rigid main body portion 70 and a relatively resilient ligating portion 72 that collectively define the ligating member 14. In one embodiment, the main body portion 70 may be made from the same material as the bracket body 12, including without limitation, various metal and ceramic materials. Alternatively, the main body portion 70 may be made from a relatively rigid material different than the material of the bracket body 12. The main body portion 70 is configured to engage the bracket body 12 when the ligating member 14 is at least in the closed position. It is believed that the rigidity of the main body portion 70 may enhance the securement of the ligating member 14 to the bracket body 12 relative to the level of securement which might be otherwise achieved with a resilient or more flexible body engagement portion.

Figure 2:
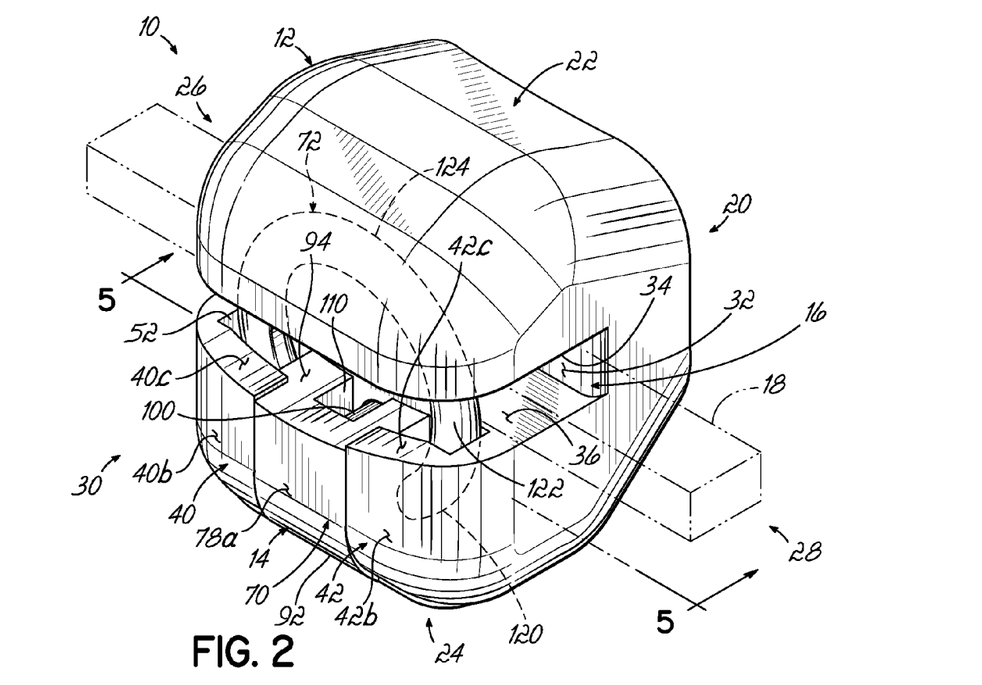
FIG. 2 is a perspective view of the self-ligating orthodontic bracket of FIG. 1, illustrating the ligating member of the bracket in a closed position.

The main body portion 70 includes a mesial portion 74, a distal portion 76, and a central portion 78 intermediate the mesial and distal portions 74, 76. At least in the closed position, projections 40, 42 generally overlie mesial and distal portions 74, 76, respectively, and central portion 78 projects in the labial direction such that the labial surface 78a of central portion 78 is substantially aligned with or flush with the labial surface 40b, 42b of projections 40, 42 (FIG. 2). Such a configuration essentially defines gingival-occlusal directed tracks or grooves 80, 82 in the labial surface of the ligating member 14 along which projections 40, 42 move as the ligating member 14 is moved between the opened and closed positions.

The resilient ligating portion 72 is coupled to the main body portion 70 and is configured to overlie the archwire slot 16 when the ligating member 14 is in the closed position. The ligating portion 72 may be formed from a resilient material that provides the ligating portion 72 with some level of flexibility or resiliency such that ligating portion 72 is sufficiently deformable. In one embodiment, for example, the ligating portion 72 may be formed from a superelastic material, such as nickel titanium (NiTi), or other suitable metals or plastics that provide a desired level of resiliency. As illustrated in the figures, in an exemplary embodiment, the ligating portion 72 may be configured by forming a generally elongate member (e.g., wire, rod, etc.) into a certain geometrical shape. By way of example, the ligating portion 72 may have a generally circular loop or ring configuration. Other geometries are possible however. For instance, as illustrated in FIGS. 6A-6C, the ligating portion 72 may be configured as a square (FIG. 6A), rectangular (FIG. 6B), or triangular (FIG. 6C) loop.

Figure 6:
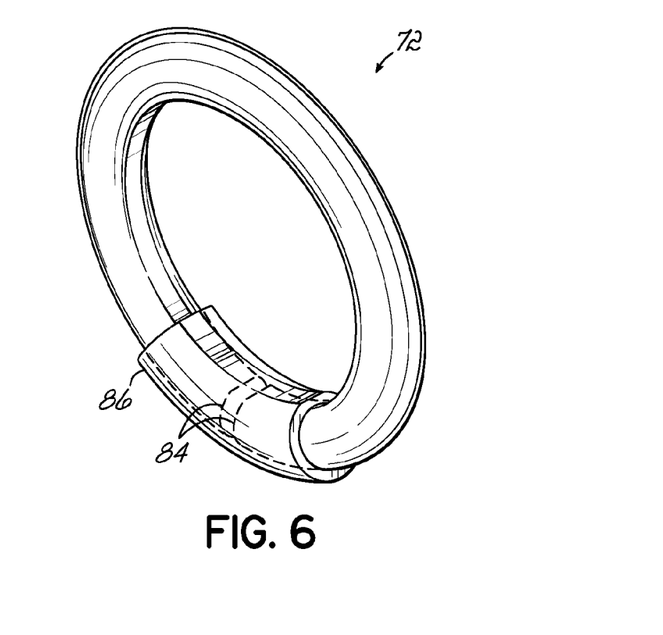
FIG. 6 is a perspective view of a ligating portion of the ligating member in accordance with one embodiment of the invention.
Figure 6A:
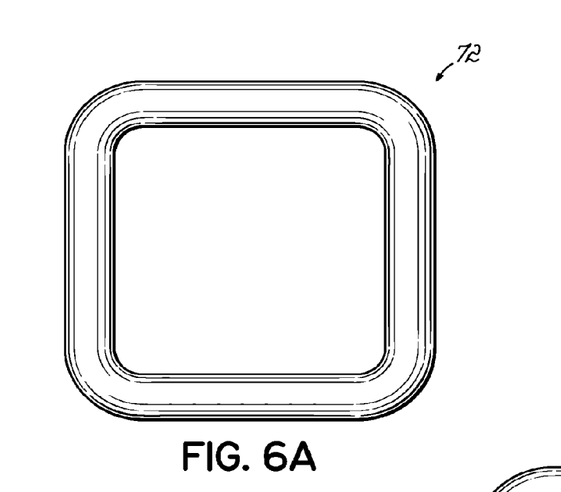
FIG. 6A is a perspective view of a ligating portion of the ligating member in accordance with another embodiment of the invention.
Figure 6B:
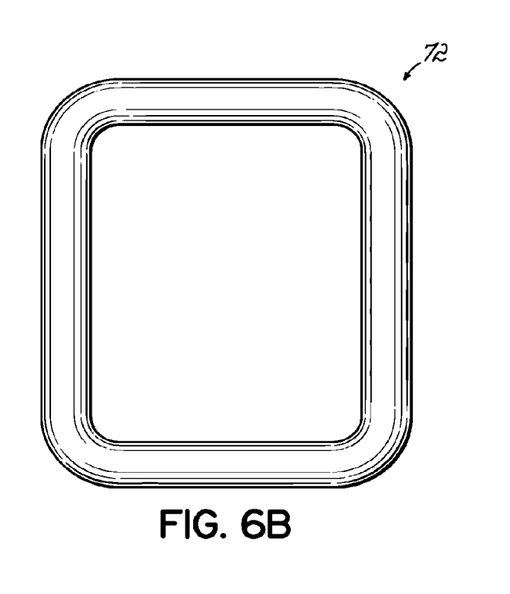
FIG. 6B is a perspective view of a ligating portion of the ligating member in accordance with yet another embodiment of the invention.
Figure 6C:
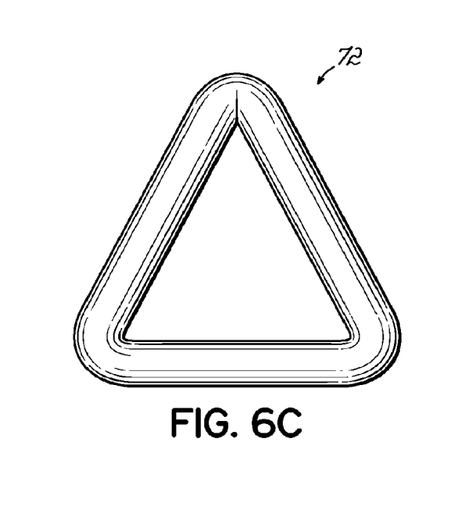
FIG. 6C is a perspective view of a ligating portion of the ligating member in accordance with yet another embodiment of the invention.
Figure 7:
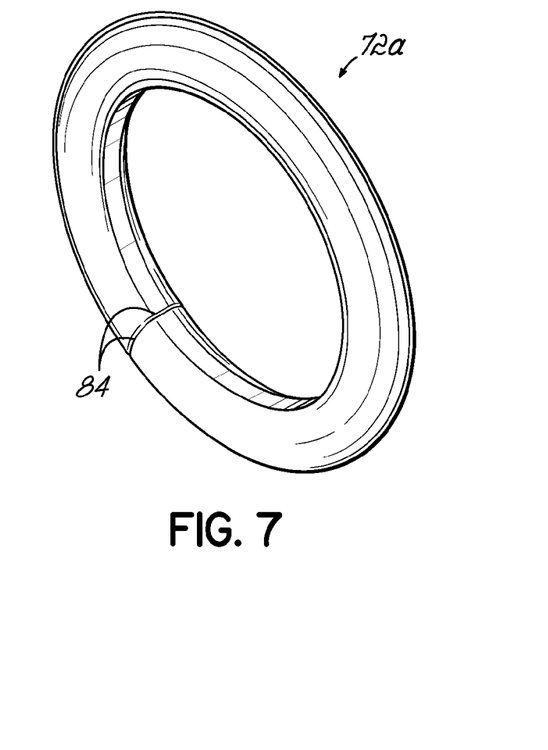
FIG. 7 is a perspective view of a ligating portion of the ligating member in accordance with another embodiment of the invention.
Figure 8:
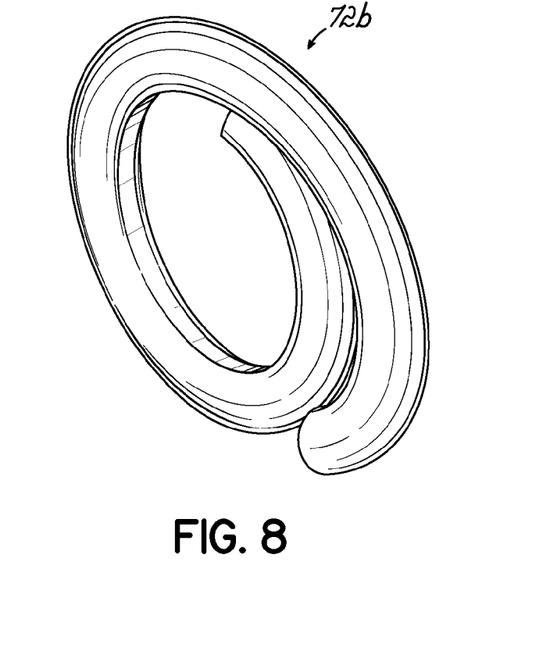
FIG. 8 is a perspective view of a ligating portion of the ligating member in accordance with yet another embodiment of the invention.

With reference to FIGS. 6-8, the resilient ligating portion 72 may be formed by several different methods. As shown in FIG. 6, in one embodiment, the ligating portion 72 may be formed by joining longitudinal ends 84 of the ligating portion 72 to a connector 86. As noted above, the ligating portion 72 may be made out of an elongate member that is joined to connector 86, which may take the form of a sleeve or collar, to define the ligating portion 72. The sleeve or collar may be made of a suitable metal, plastic, or ceramic material, for example. Other materials may also be possible. The particular material and configuration of the connector 86 may be selected to provide the overall shape to the ligating portion 72 (e.g., circular) and to facilitate coupling of the ligating portion 72 to the main body portion 70 (e.g., minimize stress concentrations, material degradation, promote bonding, etc.).

As shown in FIG. 7, in an alternative embodiment the ligating portion 72a may be formed by directly joining the longitudinal ends 84 of the ligating portion 72a to one another using bonding materials and/or other techniques, such as spot welding, to close the loop of the ligating portion 72. This may obviate the need to use a separate connector to facilitate coupling to the main body portion 70. However, it should be recognized that a connector, such as connector 86, may also be used in this embodiment as well. In yet another embodiment, as illustrated in FIG. 8, the ligating portion 72b may be formed by wrapping a wire or other elongated member in a set of at least partially overlapping loops in a keychain-like manner. For clarity, FIG. 8 illustrates part of the overlapping region being separated or flexed away from each other. However, it should be recognized that much like a keychain, the ligating portion 72b will have a closed loop configuration under normal conditions.

Figure 1:
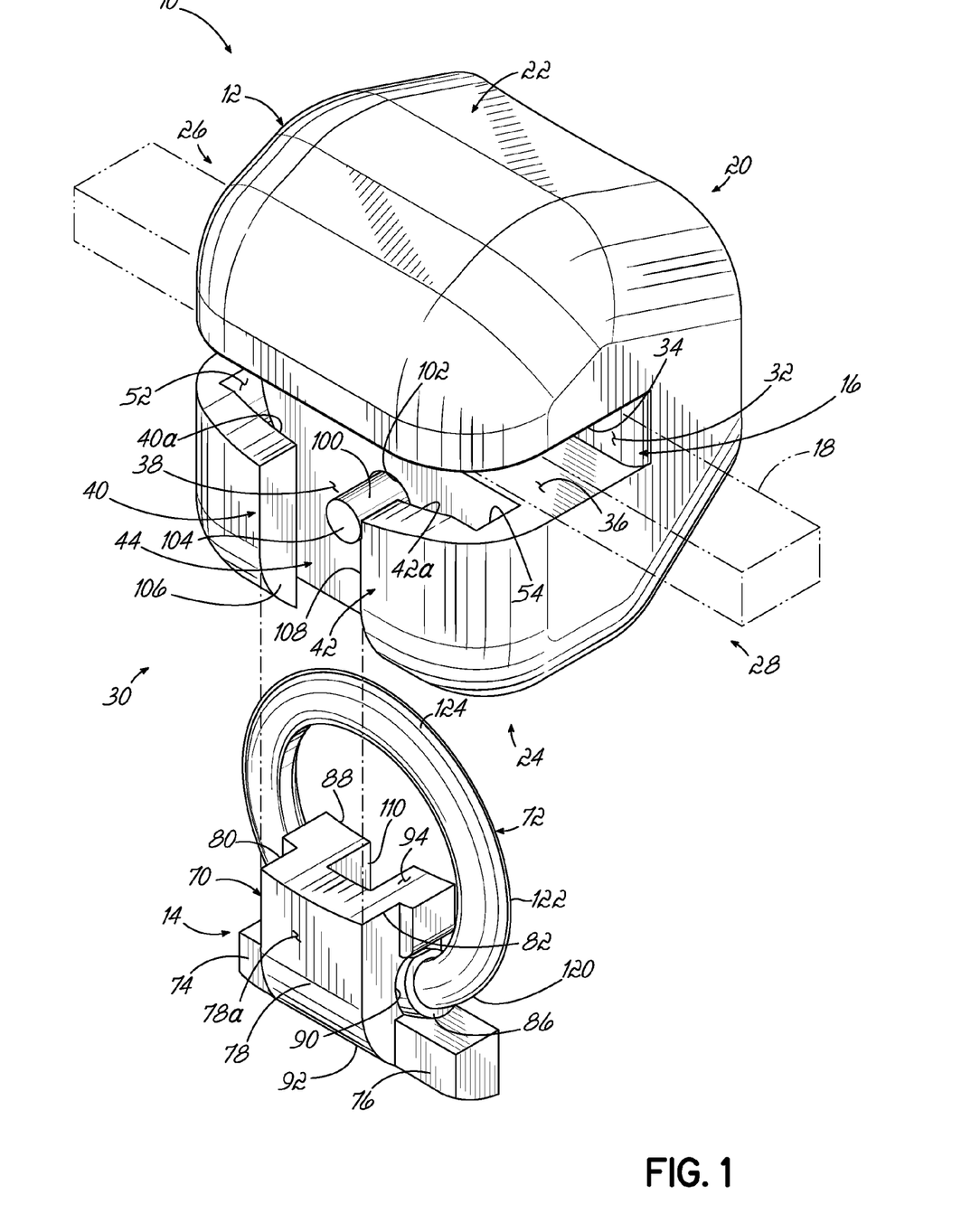
FIG. 1 is a disassembled perspective view of a self-ligating orthodontic bracket in accordance with one embodiment of the invention.
Figure 3:
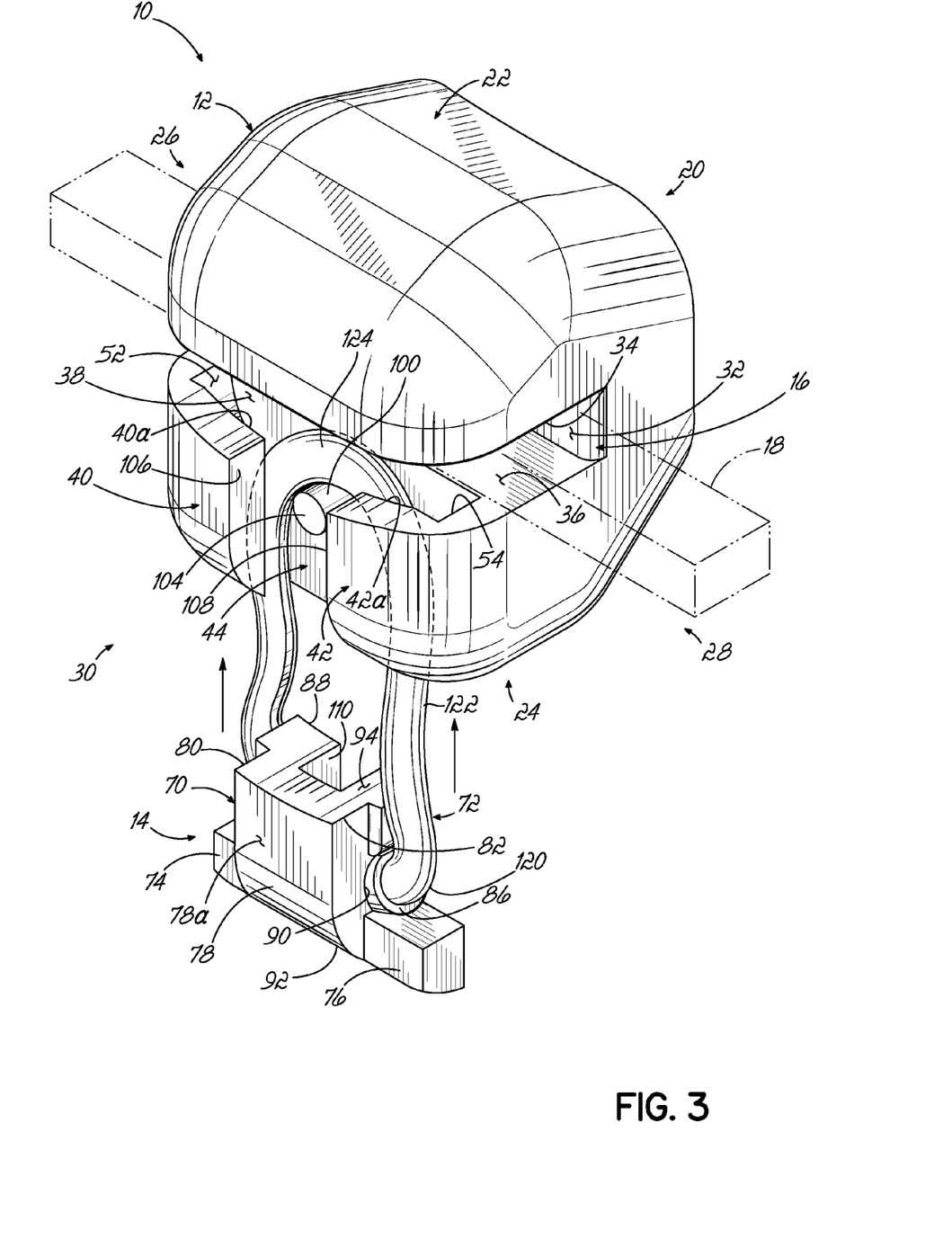
FIG. 3 is a perspective view of the self-ligating orthodontic bracket of FIG. 1, illustrating the ligating member of the bracket in an opened position.

In reference to FIGS. 1 and 3, to couple the ligating portion 72 to the main body portion 70, the lingual surface 88 of main body portion 70 may include a groove 90 configured to receive at least a portion of the ligating portion 72. The groove 90 may have an arcuate shape in cross section and may have a mesial-distal shape corresponding to the shape of the ligating portion 72 (e.g., circular arc for a ligating portion 72 configured as a circular ring). The section of the ligating portion 72 received in groove 90 may be secured therein through any suitable means including, without limitation, bonding, welding, friction fit or other suitable processes. As noted above, depending on the particular materials of the main body portion 70 and the ligating portion 72, the connector 86 may facilitate this coupling.

The groove 90 is generally disposed between the gingival and occlusal surfaces 92, 94 of the main body portion 70 so as to bifurcate the mesial and distal portions 74, 76 into occlusal portions and distal portions. Additionally, the labial-lingual dimension of the ligating portion 72 must be such as to allow the ligating portion 72 to fit within the guiding track 44. For example, in one embodiment, the labial-lingual width of the ligating portion 72 may be less than or equal to the labial-lingual width of the mesial and distal portion 74, 76 of ligating member 14. This would allow the main body portion 70 to be inserted into the guiding track 44 unimpeded by the coupling between the ligating portion 72 and the main body portion 70.

As shown in FIGS. 1, 3 and 4, the orthodontic bracket 10 includes a retaining mechanism that retains the ligating member 14 to the bracket body 12 when the ligating member 14 is in the opened position (FIG. 3). In other words, the retaining mechanism prevents the ligating member 14 from becoming separated from the bracket body 12 when in the opened position. In one embodiment, the retaining mechanism includes an elongate, relatively rigid retaining pin 100 projecting labially from a bore 102 formed in support surface 38 and configured to securely receive a portion of the pin 100 therein. The retaining pin 100 may be formed from a suitable material including various metals or plastics and be secured within bore 102 through various processes including bonding, staking, welding, etc. Additionally, the retaining pin 100 may be solid or a tubular member (not shown). While the retaining pin 100 is shown as being circular in cross section, it should be recognized that other cross sectional shapes are possible. The bore 102 may be a blind bore such that the retaining pin 100 must be inserted into the bore 102 through the labial side 30 of bracket body 12. Alternatively, the bore 102 may extend through the bracket body 12 such that the retaining pin 100 may be inserted from the lingual side 20 of bracket body 12. The bore 102 generally has a cross-sectional shape corresponding to the cross-sectional shape of the retaining pin 100.

The retaining pin 100 extends from support surface 38 at a location gingivally from archwire slot surface 36 and generally centrally between projections 40, 42. To facilitate retention of the ligating member 14 to the bracket body 12, the retaining pin 100 should extend away from support surface 38 such that a terminating end 104 of the retaining pin 100 is generally aligned with or adjacent to the lingual surfaces 40a, 42a of projections 40, 42. Additionally, as best shown in FIG. 3, the gap between the inner edges 106, 108 of projections 40, 42 and the retaining pin 100 should be less than a thickness of the elongate member (e.g., wire or rod) that forms ligating portion 72.

As best shown in FIG. 3, the retaining pin 100 is configured to extend through the ligating portion 72 of ligating member 14, which can be done during assembly of the ligating member 14 to bracket body 12, so that when in the opened position, the ligating portion 72 cannot slip past the retaining pin 100 and thereby come away from bracket body 12. To accommodate the retaining pin 100 when the ligating member 14 is in the closed position, the lingual surface 88 of the main body portion 70 may include a notch 110 that is open to the occlusal surface 94 thereof and sized to receive the retaining pin 100 therein as the ligating member 14 is moved toward the closed position.

Now that the various features of orthodontic bracket 10 have been described in sufficient detail, attention will now be turned to describing its operation. For purposes of discussion, the description starts with the ligating member 14 in the closed position (FIG. 2). In the closed position, the main body portion 70 is generally disposed in the guiding track 44 such that the occlusal surface 94, gingival surface 92, and labial surface 78a thereof is generally substantially aligned with or flush with the occlusal surface 40c, 42c, gingival surface 40d, 42d (FIG. 4), and labial surface 40b, 42b of the projections 40, 42, respectively. This provides the labial side and the gingival side of the assembled orthodontic bracket 10 with a relatively smooth topology. Additionally, the retaining pin 100 is disposed in the notch 110 in main body portion 70 in the closed position.

When in the closed position, a gingival section 120 of the ligating portion 72 is disposed in the arcuate portion 44b of guiding track 44; an intermediate section 122 extends across the archwire slot 16 and is configured to retain the archwire 18 in archwire slot 16; and an occlusal section 124 extends above the archwire slot 16 and into retaining recess 60. When in the closed position, the hybrid nature of the ligating member 14, and more particularly the resilient nature of the ligating portion 72, and/or the particular configuration of the ligating portion 72 (e.g., circular ring) may provide certain benefits to orthodontic bracket 10.

In this regard, forming ligating portion 72 from a resilient material may facilitate the uniform distribution of forces acting between the ligating portion 72 and the bracket body 12. By way of example, a resilient ligating portion 72 may allow the surfaces of the ligating portion 72 to deform so as to conform to imperfections on confronting surfaces of the bracket body 12 when they come into contact during use. More particularly, the occlusal section 124 of resilient ligating portion 72 may conform to imperfections associated with either of surfaces 62, 64, 66 of retaining recess 60 and more uniformly distribute forces acting between the ligating portion 72 and those surfaces of recess 60. In this manner, the forces acting between the ligating portion 72 and the retaining recess 60 may, for example, be distributed along a substantial portion or even the entirety of surfaces 62, 64, 66, rather than at selected locations on those surfaces, thereby reducing point loading on the bracket body 12. This interaction may become important when the archwire 18 does not fit nicely within the archwire slot 16 and pushes against the ligating portion 72, causing it to contact recess surface 62. A similar interaction may also exist between the ligating portion 72, and more particularly gingival section 120, and the lingual surfaces 40a, 42a of projections 40, 42.

A more uniform distribution of forces allows bracket manufacturers to reduce the required size of the bracket body 12 by virtue of the fact that the bracket body 12 is subject to lower peak stress concentrations. This may be especially beneficial for ceramic orthodontic brackets, which tend to be more brittle than their metal counterparts, and therefore bulkier in their design so as to withstand the design loads. In addition, smaller orthodontic brackets improve patient comfort and provide desirable aesthetics that, in turn, improve overall patient satisfaction.

The particular configuration of ligating portion 72 may provide certain benefits during orthodontic treatment as well. By way of example, the ringed configuration may provide two-point contact between the ligating member 14 and the archwire 18 that enhances rotational control during treatment. More particularly, as illustrated in FIG. 2, the intermediate section 122 of ligating portion 72 covers or extends across the archwire slot 16 at only two spaced-apart locations and thereby can make contact with the archwire 18 at only these two locations. As more fully explained in commonly owned U.S. application Ser. No. 12/689,145, filed Jan. 18, 2010, the disclosure of which is hereby incorporated by reference herein in its entirety, this spaced-apart two point contact increases the moment arms acting on the bracket body 12 (from the archwire 18) and makes the contact location more predictable. Additionally, the resilient nature of ligating portion 72, and more particularly intermediate section 122, also facilitates a more uniform distribution of forces acting between the ligating portion 72 and the archwire 18. Again, more uniformly distributing forces lowers peak stress concentrations which, in turn, may improve dimensional aspects of the ligating member 14 and/or bracket body 12.

One of the more interesting aspects of the present design, however, is the interaction between the gingival section 120 of ligating portion 72 and the undercut design of arcuate portion 44b of guiding track 44. As best shown in FIG. 5, when in the closed position, the ligating portion 72 is in a generally expanded state (e.g., undeformed or slightly compressed state) such that the ligating portion 72 has a mesial-distal cross dimension (e.g., outer diameter of circular ring) substantially equal to or slightly less than a maximum mesial-distal cross dimension of the arcuate portion 44b (e.g., adjacent archwire slot surface 36), but greater than the mesial-distal cross dimension of the constant width portion 44a. In this way, the ligating portion 72 may be relatively freely seated within arcuate portion 44b and engage projecting mesial and distal walls 52, 54. In the particular embodiment shown, the walls 52, 54 that form arcuate portion 44b have a radius of curvature substantially equal to or slightly greater than a radius of curvature of the outer periphery of the circular ring that forms ligating portion 72. Depending on the particular geometry of ligating portion 72 (at least along gingival section 120) mesial and distal walls 52, 54 may have other configurations.

When the ligating member 14 is in the closed position and the gingival section 120 of ligating portion 72 is seated within arcuate portion 44b, the interaction between the ligating portion 72 and the walls 52, 54 provides a threshold level of resistance to any movement of the ligating member 14 away from the closed position and toward the opened position. However, if a sufficiently large opening force is applied to the ligating member 14 in, for example, the gingival direction, the interaction between the walls 52, 54 and ligating portion 72 causes the ligating portion 72 to start flexing or deforming toward a contracted state or contracted position. This interaction causes the ligating portion 72 to generally contract in a mesial-distal direction and generally expand in a gingival-occlusal direction (e.g., become more elliptical). Alternatively or additionally, instead of expanding in the gingival-occlusal direction, the ligating portion 72 may buckle along a gingival-occlusal mid section. With a sufficient amount of contraction in the mesial-distal direction, the mesial-distal cross dimension of ligating portion 72 will be substantially equal to the mesial-distal cross dimension of constant width portion 44a and allow the ligating portion 72 to pass into constant width portion 44a. The ligating member 14 may then be moved gingivally toward the opened position with the application of a sufficient force. As the ligating member 14 moves toward the opened position, the main body portion 70 may become disengaged from the bracket body 12 (FIG. 3). However, as discussed above, the retaining pin 100 prevents the ligating portion 72 from passing therebeyond, thereby preventing the ligating member 14 from becoming completely separated from the bracket body 12.

Once an archwire 18 is inserted into the archwire slot 16, such as during an initial installation or a change out of the archwire 18, the ligating member 14 may be moved back toward the closed position. Although the ligating portion 72 may be continuously biased back toward its expanded position, it is not able to do so until the ligating portion 72 reaches or nearly reaches the closed position, wherein the ligating portion 72 is free of the constant width portion 44a and snaps back out to its generally expanded position so as to be seated in the arcuate portion 44b as shown in FIG. 5.

The particular configuration of the guiding track 44 (e.g., the undercut configuration of the guiding track 44) and the configuration of the ligating portion 72 (e.g., circular ring) cooperate in a manner that provides a mechanism for selectively maintaining the ligating member 14 in the closed position. In one aspect of the invention, a tool (not shown) may be used to apply the threshold level of force to the ligating member 14 so as to move the ligating member toward the opened position. In this regard, due to the particular design of the ligating member 14, the tool may be inserted directly into the archwire slot 16, which represents a relatively large target to the orthodontist when attempting to open the ligating member 14. More particularly, a tool may be inserted into the archwire slot 16 and twisted such that one aspect of the tool engages the archwire slot surface 34 and another aspect of the tool engages the occlusal surface 94 of the main body portion 70. It is because the occlusal surface 94 of main body portion 70 does not extend above the archwire slot 16 that the archwire slot 16 may be utilized in this manner. Additionally, such a design obviates the need for a separate tool receptacle in bracket body 12.

Figure 9:
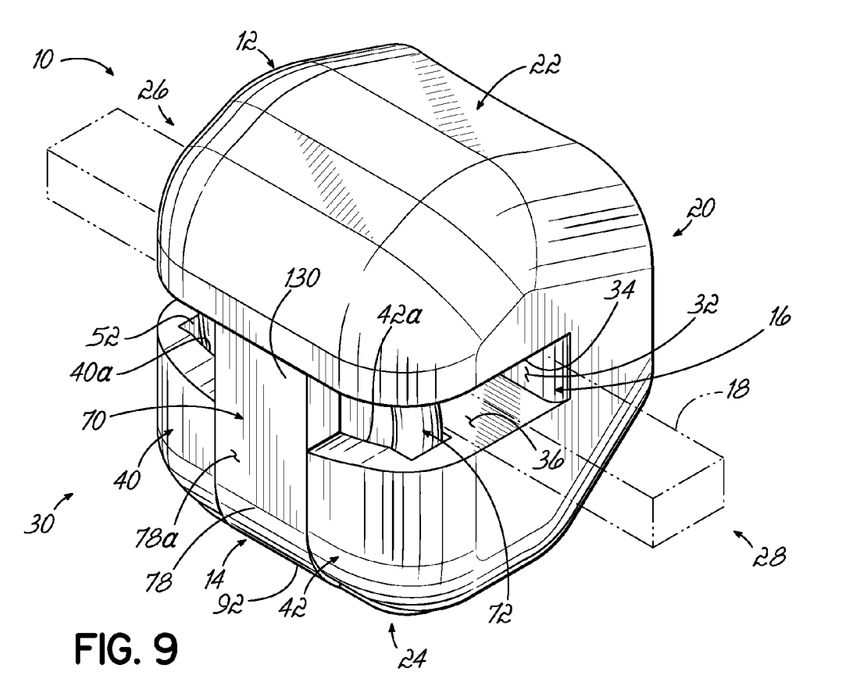
FIG. 9 is a perspective view of a self-ligating orthodontic bracket similar to FIGS. 1-3, but with a ligating member in accordance with another embodiment of the invention.

As illustrated in FIG. 9, however, in an alternative embodiment, the main body portion 70 may include an extension member 130 extending occlusally from surface 94. When the ligating member 14 is in the closed position, the extension member 130 is configured to extend across the archwire slot 16 so as to be adjacent to or in engagement with slot surface 34. Moreover, the extension member 130 may also allow the main body portion 70 to remain coupled to the bracket body 12 when in the opened position (not shown).

In yet another aspect in accordance with embodiments of the invention, the ligating member 14 may be configured for either passive ligation or active ligation. For example, in the embodiment shown in FIG. 2, the ligating portion 72 of ligating member 14 may be configured to simply block the opening to the archwire slot 16 without imposing any biasing force on the archwire 18 that forces the archwire toward the base surface 32. Such a configuration constitutes passive ligation and may be particularly beneficial during the early stages of orthodontic treatment.

Figure 10:
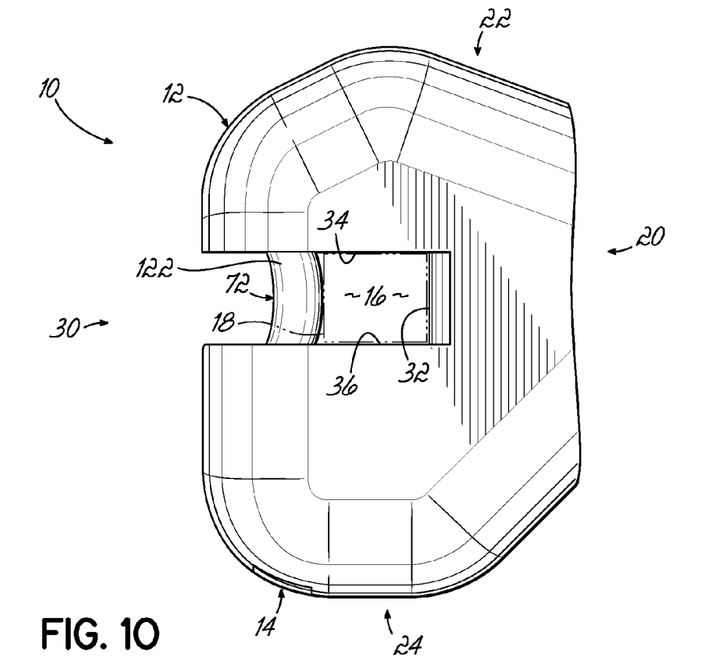
FIG. 10 is a side view of a self-ligating orthodontic bracket similar to of FIGS. 1-3 illustrating active ligation.

In an alternative embodiment, and as illustrated in FIG. 10, the ligating portion 72 of ligating member 14 may be configured for active ligation wherein the ligating portion 72 imposes a biasing force on the archwire 18 toward the base surface 32 of the archwire slot 16. In this regard, the ligating portion 72 may be suitably shaped so as to engage the archwire 18 when the ligating member 14 is in the closed position. More particularly, the ligating portion 72 may have a concave shape such that the intermediate section 122 of ligating portion 72 engages the archwire 18 and pushes it toward base surface 32 of archwire slot 16. Of course in such an embodiment, the ligating portion 72 is capable of flexing or deforming such that the ligating member 14 may be moved between the opened and closed positions.

As discussed above, the securing mechanism that secures the ligating member 14 in the closed position includes a portion of the ligating member 14 and a portion of the guiding track 44 that cooperate in a manner that achieves the securing function. More specifically, the cooperation between the two parts is made possible by the undercut design in the guiding track 44 (e.g., arcuate portion 44b). As noted above, such an undercut design is generally not possible in conventional orthodontic bracket manufacturing processes, such as the MIM and CIM processes, due to the single shot molding process typically utilized as part of manufacturing the orthodontic brackets. In accordance with another aspect of the invention, a method of making orthodontic bracket 10 having undercuts in the bracket body 12 is disclosed. In a particular advantageous aspect, the undercuts may be formed in the bracket body 12 during the formation of the bracket body 12 and costly and time-consuming post-formation processes may be significantly reduced or eliminated all together.

Figure 11:
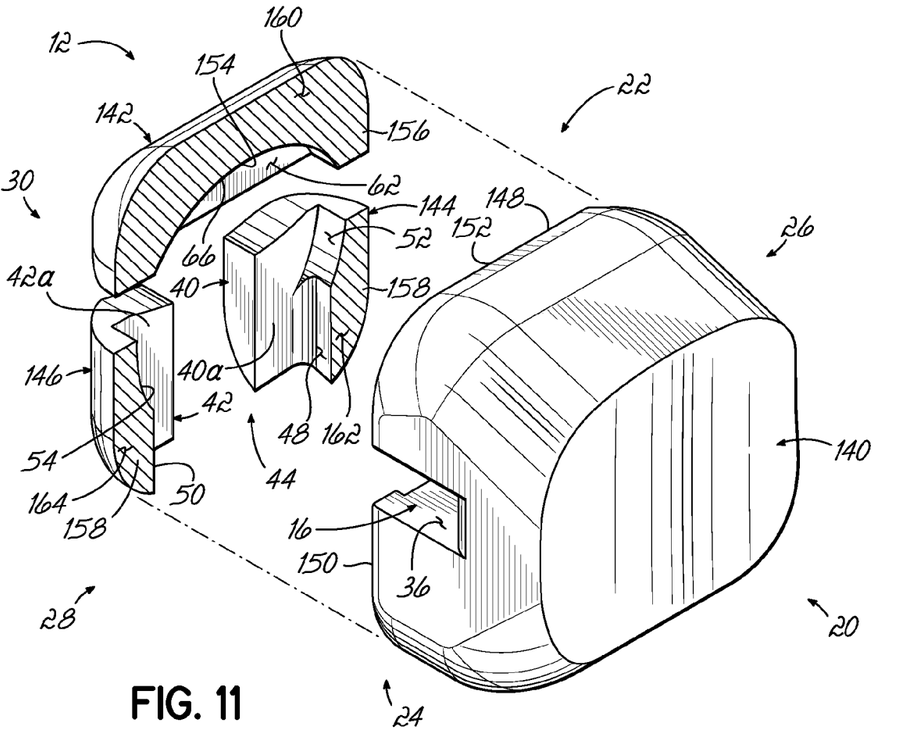
FIG. 11 is a diagrammatic illustration of a method of manufacturing the bracket body of the orthodontic bracket shown in FIGS. 1-3.

One aspect of the inventive method is illustrated in FIG. 11. As noted previously and with reference to FIGS. 4 and 11, the guiding track 44 and the retaining recess 60 may align along a generally common plane such that the support surface 38 and the recess surface 64 generally lie along the common plane. In reference now to FIG. 11, if one imagines this plane passing through the bracket body 12, it would separate the bracket body into four distinct parts 140, 142, 144, 146. The first part 140 forms the bulk of the bracket body 12 and includes a major portion of the archwire slot 16. However, the labial side 148 of part 140 has a generally planar gingival surface 150 and a generally planar occlusal surface 152. As can be appreciated, a portion of planar gingival surface 150 forms support surface 38 and a portion of planar occlusal surface 152 forms recess surface 64 (depicted in FIG. 4). The second part 142 generally forms the juncture between the occlusal side 22 and labial side 30 of bracket body 12. Part 142 includes a cavity 154 in its lingual side 156 that ultimately forms recess surfaces 62 and 66. The third and fourth parts 144, 146 essentially include the projections 40 and 42. The lingual side 158 of these parts defines surfaces 40a, 42a and walls 48, 50, 52, 54.

In accordance with aspects of the inventive method, the orthodontic bracket 10 may still be formed through a MIM or CIM process. However, the bracket 10 is not formed in a single shot molding process. Instead, each part 140, 142, 144, 146 is separately molded, for example, in different molding apparatus. Each of these molding processes includes injecting a mixture of sinterable particles and binder into the dedicated molding apparatus. The sinterable particles may be metal particles or powder for the MIM process and ceramic particles or powder for the CIM process. This process is generally understood in the orthodontic art and will not be explained in further detail. For example, details of such processes may be found in U.S. application Ser. No. 11/193,571, filed Jul. 29, 2005, the disclosure of which is incorporated by reference herein in its entirety. Nevertheless, what results from these molding processes is the four separate parts 140, 142, 144, 146 in a green state.

An interesting aspect of this method, however, is the realization that there are no undercut formations in any of the four parts 140, 142, 144, 146. Thus, the features in the various parts 140, 142, 144, 146, including, for example, the archwire slot 16 in part 140, the cavity 154 in part 142, or the walls 48, 50, 52, 54 in parts 144, 146, may be suitably formed in a single shot molding process without any post-formation processing. As known from above, however, when these parts 140, 142, 144, 146 are assembled, undercut formations which could not otherwise be formed in a single shot molding process result.

When in the green state, the parts 140, 142, 144, 146 are still relatively soft and pliable and thus suitable for further assembling. In this regard, the separate parts 140, 142, 144, 146 may be assembled in order to form a green intermediate body having the shape of orthodontic bracket 10. More particularly, part 142 includes a generally planar engagement face 160 configured to be mated to the planar occlusal surface 152 of part 140. For example, the tackiness of the green parts may allow parts 140, 142 to be suitably mated. Those of ordinary skill in the art may recognize other means for at least temporarily mating parts 140, 142. Similarly, parts 144, 146 include generally planar engagement faces 162, 164 configured to be mated to planar gingival surface 150 of part 140.

With parts 142, 144, 146 now mated to part 140 as described above, the intermediate green body having a shape of orthodontic bracket 10 results. To form the orthodontic bracket 10, the intermediate green body is sintered. The sintering process is generally known in the art and will not be explained in further detail herein. Again, U.S. application Ser. No. 11/193,571 discloses various sintering processes and is incorporated by reference herein in its entirety. Nevertheless, it should be recognized that the interfaces, should any exist, between parts 140, 142, 144, 146 substantially disappear during the sintering process and a metal or ceramic sintered body results substantially without any discontinuities or other voids or defects occurring at the mating surfaces.

Although mentioned above, the final orthodontic bracket 10 has undercut formations, namely the undercuts that result in arcuate portion 44*b* and the retaining recess 60, which were not formed through post-formation processes, but which were instead formed during the formation of the bracket body itself. Each part 140, 142, 144, 146 that ultimately formed the green intermediate body had features which did not have undercut formations. Thus, each part could be formed in a single shot molding process. However, when the parts 140, 142, 144, 146 were assembled, the features on the various parts cooperated with features or portions on another part such that the green intermediate body had undercut formations therein. These undercut formations are retained in the final orthodontic bracket 10. As discussed above, these undercut formations allow orthodontic bracket 10 to operate in new and interesting ways.

Aspects of the method should not be limited to the particular embodiment described above. For example, in the embodiment above, the bracket body 12 was divided into four separate parts for the purpose of creating undercuts when the four parts were assembled into a single body. However, it is within the scope of the present invention that an orthodontic bracket may be divided into two or more bodies and assembled to form an intermediate green body to provide other benefits which might not be otherwise achievable by forming the intermediate green body in a single shot molding process or by some other process. That intermediate green body may then be sintered to result in an orthodontic bracket having certain beneficial features. Thus, the inventive aspects of the method may be broader than that described above.

While the present invention has been illustrated by a description of various preferred embodiments and while these embodiments have been described in some detail, it is not the intention of the inventor to restrict or in any way limit the scope of the appended claims to such detail. Additional advantages and modifications will readily appear to those skilled in the art. For example, while the ligating member has been described herein as having a main body portion and a resilient ligating portion, in an alternative embodiment, the main body portion may be omitted such that the resilient ligating portion forms a substantial portion, if not the entirety, of the ligating member. The various features of the invention may be used alone or in any combinations depending on the needs and preferences of the user.

What is claimed is:

1. An orthodontic bracket, comprising:
a bracket body configured to be mounted onto a tooth, the bracket body including an archwire slot having a base surface and opposed slot surfaces projecting substantially perpendicularly from the base surface and being adapted to receive an archwire therein, the bracket body further including a support surface intersecting one of the opposed slot surfaces, a pair of opposing projections extending outwardly from the support surface, the support surface and opposing projections defining a guiding track having a first portion and a second portion having a width between opposing projections greater than a width between opposing projections of the first portion, the first portion being spaced apart from the archwire slot by the second portion; and
a ligating member coupled to the bracket body and movable relative thereto in the guiding track between an opened position in which the archwire is received into the archwire slot, and a closed position in which the ligating member overlies the archwire slot and retains the archwire in the archwire slot, the ligating member having a relatively rigid main body portion and a resilient ligating portion, the resilient ligating portion overlying the archwire slot when in the closed position,
wherein the resilient ligating portion is capable of flexing between an expanded position and a contracted position, the resilient ligating portion being in the expanded position when in the second portion of the guiding track and being in the contracted position when in the first portion of the guiding track, wherein moving the ligating member toward the opened position applies a force to the resilient ligating portion causing the resilient ligating portion to deform to the contracted position so as to fit within the first portion of the guiding track.

2. The orthodontic bracket of claim 1, wherein the first portion of the guiding track has a generally constant width, and the second portion of the guiding track has a variable width.

3. The orthodontic bracket of claim 2, wherein the variable width of the second portion is narrowest at an intersection of the first portion and the second portion and the variable width is greatest at an intersection of the second portion with the archwire slot.

4. The orthodontic bracket of claim 1, wherein the guiding track has a Y-shaped configuration.

5. The orthodontic bracket of claim 1, wherein the second portion has an arcuate shape such that the width of the second portion is greatest at the intersection of the guiding track with the archwire slot.

6. The orthodontic bracket of claim 1, wherein the guiding track is configured to interfere with the ligating portion to provide a threshold level of resistance to movement of the ligating member away from the closed position toward the opened position.

7. The orthodontic bracket of claim 1, wherein the ligating portion is a generally elongate member formed in a closed geometrical shape.

8. The orthodontic bracket of claim 7, wherein, when in the expanded position, the closed geometrical shape is at least one of a ring, square, rectangle, and triangle.

9. The orthodontic bracket of claim 1, wherein the ligating portion is resiliently biased toward the expanded position.

10. The orthodontic bracket of claim 1, wherein the ligating member is configured to deform from the expanded position to the contracted position when the ligating member is moved from the closed to the opened position.

11. The orthodontic bracket of claim 1, wherein the ligating portion is configured to impose a biasing force on the archwire.

12. The orthodontic bracket of claim 1, wherein the shape of the ligating portion in the contracted position is different from the shape of the ligating member in the expanded position.

13. The orthodontic bracket of claim 1, further comprising:
a retaining mechanism for retaining the ligating member to the bracket body when the ligating member is in the opened position.

14. The orthodontic bracket of claim 13, wherein the retaining mechanism includes a retaining pin coupled to the bracket body, and the ligating portion forms a ring, the retaining pin contacting the ring when the ligating member is in the opened position.

15. The orthodontic bracket of claim 1, wherein the bracket body includes a retaining recess opposite of, and separated by the archwire slot from, the guiding track, the retaining recess being configured to receive a portion of the ligating member when in the closed position.

16. The orthodontic bracket of claim 15, wherein a shape of the retaining recess includes a substantially constant radius of curvature and a section of the ligating member conforms to that shape.

17. The orthodontic bracket of claim 1, wherein the main body of the ligating member includes an extension member that extends substantially across the archwire slot, the ligating portion being positioned between the bracket body and the extension member when the ligating member is in the closed position.

18. The orthodontic bracket of claim 1, wherein the ligating portion is in the expanded position when the ligating member completely overlies the archwire slot.

19. An orthodontic bracket, comprising:
a bracket body configured to be mounted onto a tooth, the bracket body including an archwire slot having a base surface and opposed slot surfaces projecting substantially perpendicularly from the base surface and being adapted to receive an archwire therein, the bracket body further including a support surface intersecting one of the opposed slot surfaces, a pair of opposing projections extending outwardly from the support surface, the support surface and opposing projections defining a guiding track having a first portion and a second portion having a width between opposing projections greater than a width between opposing projections of the first portion; and
a ligating member coupled to the bracket body and movable relative thereto in the guiding track between an opened position in which the archwire is received into the archwire slot, and a closed position in which the ligating member overlies the archwire slot and retains the archwire in the archwire slot, the ligating member having a relatively rigid main body portion and a resilient ligating portion, the resilient ligating portion overlying the archwire slot when in the closed position,
wherein the resilient ligating portion is capable of flexing between an expanded position and a contracted position, the resilient ligating portion being in the expanded position when in the second portion of the guiding track and being in the contracted position when in the first portion of the guiding track, wherein moving the ligating member toward the opened position applies a force to the resilient ligating portion causing the resilient ligating portion to deform to the contracted position so as to fit within the first portion of the guiding track,
wherein the first portion of the guiding track has a generally constant width, and the second portion of the guiding track has a variable width,
wherein the variable width of the second portion is narrowest at an intersection of the first portion and the second portion and the variable width is greatest at an intersection of the second portion with the archwire slot.

20. An orthodontic bracket, comprising:
a bracket body configured to be mounted onto a tooth, the bracket body including an archwire slot having a base surface and opposed slot surfaces projecting substantially perpendicularly from the base surface and being adapted to receive an archwire therein, the bracket body further including a support surface intersecting one of the opposed slot surfaces, a pair of opposing projections extending outwardly from the support surface, the support surface and opposing projections defining a guiding track having a first portion and a second portion having a width between opposing projections greater than a width between opposing projections of the first portion; and
a ligating member coupled to the bracket body and movable relative thereto in the guiding track between an opened position in which the archwire is received into the archwire slot, and a closed position in which the ligating member overlies the archwire slot and retains the archwire in the archwire slot, the ligating member having a relatively rigid main body portion and a resilient ligating portion, the resilient ligating portion overlying the archwire slot when in the closed position,
wherein the resilient ligating portion is capable of flexing between an expanded position and a contracted position, the resilient ligating portion being in the expanded position when in the second portion of the guiding track and being in the contracted position when in the first portion of the guiding track, wherein moving the ligating member toward the opened position applies a force to the resilient ligating portion causing the resilient ligating portion to deform to the contracted position so as to fit within the first portion of the guiding track,
wherein the second portion has an arcuate shape such that the width of the second portion is greatest at the intersection of the guiding track with the archwire slot.

* * * * *